United States Patent [19]

Matsunaga et al.

[11] Patent Number: 4,495,173

[45] Date of Patent: Jan. 22, 1985

[54] PRE-SHAMPOO TYPE HAIR TREATMENT COMPOSITION

[75] Inventors: Kinjiro Matsunaga, Miyashiro; Takeo Okumura, Sakura; Rikio Tsushima, Wakayama, all of Japan

[73] Assignee: Kao Soap Co., Ltd., Tokyo, Japan

[21] Appl. No.: 318,878

[22] Filed: Nov. 6, 1981

[30] Foreign Application Priority Data

Nov. 28, 1980 [JP] Japan .................... 55-167863

[51] Int. Cl.$^3$ .................... A61K 7/06; A61K 47/00
[52] U.S. Cl. .................... 424/70; 514/773
[58] Field of Search .................... 424/70

[56] References Cited

U.S. PATENT DOCUMENTS

| | | | |
|---|---|---|---|
| 3,033,755 | 5/1962 | Jacobi | 424/59 X |
| 3,178,353 | 4/1965 | Scheller | 424/70 |
| 3,904,748 | 9/1975 | Eckert et al. | 424/70 |
| 3,957,065 | 5/1976 | Busch et al. | 424/359 |
| 3,958,581 | 5/1976 | Abegg et al. | 132/7 |
| 4,041,150 | 8/1977 | Karjala | 424/72 |
| 4,061,150 | 12/1977 | Dasher et al. | 132/7 |
| 4,272,515 | 6/1981 | Hofman | 424/70 |
| 4,273,760 | 6/1981 | Koehler et al. | 424/70 |
| 4,279,996 | 7/1981 | Yashioka et al. | 424/72 |
| 4,283,386 | 8/1981 | Van Scott | 424/70 |

FOREIGN PATENT DOCUMENTS

| | | | |
|---|---|---|---|
| 2940220 | 4/1980 | Fed. Rep. of Germany | 424/71 |
| 22643 | of 1907 | United Kingdom | 424/70 |
| 1111934 | 5/1968 | United Kingdom | 424/70 |
| 2061956A | 5/1981 | United Kingdom | 424/70 |

Primary Examiner—Dale R. Ore
Attorney, Agent, or Firm—Oblon, Fisher, Spivak, McClelland & Maier

[57] ABSTRACT

A pre-shampoo type hair treatment composition is described which comprises at least one decomposition derivative of keratin material selected from hydrolysates of keratin material, alkali salts of decomposition products obtained by oxidation of keratin material and alkali salts of derivatives at the thiol group of decomposition products obtained by reduction of keratin material, the at least one decomposition derivative having been dissolved or dispersed in suitable solvent.

5 Claims, No Drawings 4,495,173

PRE-SHAMPOO TYPE HAIR TREATMENT COMPOSITION

BACKGROUND OF THE INVENTION

1. Field of the Invention

This invention relates to a pre-shampoo type hair treatment composition and more particularly, to a pre-shampoo type hair treatment comprising decomposition derivatives of keratin material and cationic polymer.

2. Description of the Prior Art

Hair is very readily stained such as by soilings from outside or decomposition matters or oxides of sebum secreted from scalp. For the purpose of removing the stains, it is general to wash the hair with shampoo compositions. The shampoo compositions to be used on washing of hair comprise as their principal component surface active agents such as anionic surface active agents, amphoteric surface active agents and the like, so that when hair is washed with such compositions, not only the stains but also the sebum necessary for imparting suppleness to the hair is also washed away. The hair from which sebum has been washed away is poor to the touch and is hard to comb or brush, and is thus very difficult in handling with the attendant disadvantage that the hair is readily damaged to cause split-ends and broken hairs. In order to prevent the hair from being deteriorated accompanied by the washing of hair, there are added to shampoo compositions additives such as oils and fats or polymeric compounds to improve the styling texture of the hair which has been washed.

On the other hand, pre-shampoo type hair treatments containing oils such as liquid lanolin have recently been developed and sold in the market and gained public favor as an epoch-making article for protecting hair. That is, when hair prior to washing is applied with a pre-shampoo hair treatment and then washed as usual, damages of the hair as will be caused on washing and rising and also on finishing or styling of the hair such as drying by dryers can be prevented, thus imparting conditioning effects to the hair.

However, where hair is protectively treated with such hair treatments containing oils such as lanolin as their principal component, they show disadvantages that the styling texture becomes dull and the treated hair becomes often sticky to the touch. Accordingly, there is a demand of a further improvement and stury on these treatments.

SUMMARY OF THE INVENTION

An object of the present invention is to provide a pre-shampoo type hair treatment composition which overcomes the disadvantages of the prior art.

Another object of the invention is to provide a pre-shampoo type hair treatment composition which shows excellent hair-conditioning effects.

A further object of the invention is to provide a pre-shampoo type hair treatment composition which makes use of decomposition derivatives of kertain material which have never been employed for this purpose.

The above objects can be achieved, according to the invention, a pre-shampoo type hair treatment composition which comprises a suspension or solution, in a polar solvent, of at least one decomposition derivative of kertain material selected from the group consisting of (1) hydrolyzates of keratin material, (2) alkali salts of decomposition products obtained by oxidation of keratin material, and (3) alkali salts of derivatives at the thiol group of decomposition products obtained by reduction of keratin material. The at least one decomposition derivative is preferably used in an amount of 0.05 to 5 wt% of the pre-shampoo treatment composition. The pre-shampoo treatment composition further comprises, according to a preferred aspect of the invention, at least one cationic polymer in a predetermined amount.

DETAILED DESCRIPTION AND PREFERRED EMBODIMENTS OF THE INVENTION

The decomposition derivatives of keratin materials used in the present invention are prepared by any of methods including a method in which keratin materials are decomposed by oxidation and converted into alkali salts thereof, a method in which keratin materials are decomposed by reduction and the thiol groups are chemically modified to obtain derivatives and then they are converted into alkali salts, and a method of hydrolyzing keratin materials.

The starting keratin materials include, for example, animal hair, human hair, feather, claw, horn, hoof, scale and the like, among which wool, human hair and feather are preferably used. These keratin materials may be subjected to the oxidation or reduction reaction as they are but, if necessary, they may be cut or reduced into pieces having a suitable size, or may be subjected to pretreatments such as washing and defatting.

The decomposition of the keratin materials is conducted by any of the following methods.

(1) Oxidation and Decomposition Reaction

The oxidation of keratin materials is feasible by any of methods known per se (N. H. Leon; Textile Progress, Vol. 7, page 1 (1975). Oxidizing agents are preferably organic or inorganic ones of the type which acts electrophilically on the disulfide bonds (S—S bonds) in the keratin structure. Examples of the oxidizing agents include organic peracids, inorganic peroxo acids or their salts, permanganic acid or its salts, chromic acid or related compounds, halogens, peroxides, oxyacids or their salts and the like, among which the organic peracids such as peracetic acid, performic acid and perbenzoic acid are most preferable.

The oxidation reaction is conducted in liquid media using oxidizing agents in excess with respect to the disulfide bonds in the keratin meterial, ordinarily in amounts of two equivalents or more, preferably 4–10 equivalents of the sulfide bonds. The reaction is feasible under acidic or alkaline conditions and is preferably conducted under acidic conditions and particularly weakly acidic conditions. The reaction temperature and pressure vary depending on the types of the oxidizing agent and keratin material and are not critical. In general, room temperature is sufficient, but, if necessary, heat may be applied. Atmospheric pressure is sufficient but the reaction may be conducted under reduced pressure or under pressure.

By this, the disulfide bond of keratin material is cleft into sulfonic acid.

(2) Reduction Reaction and Chemical Modification Reaction

Reducing agents employed for reducing keratin materials are preferably organic or inoganic reducing agents of the type which serves to cleave the disulfide bond in the keratin structure into a thiol group (—SH) and generally nucleophilically acts on the disulfide bond. Examples of the reducing agents include organic reducing agents such as mercaptoethanol, thioglycollic acid, benzylmercaptan, 1,4-dithiothreitol, tributylphosphine and the like, and inorganic reducing agents such as sodium hydrogensulfite, sulfides such as sodium hydrosulfide, metallic hydrides such as lithium aluminum hydride.

The amount of the reducing agent is usually in the range of 2-10 equivalents of the disulfide bonds in keratin material. The pH of the reaction system is in the range of 2-12, preferably 6-11. Outside the range, the hydrolysis undesirably takes place at the same time. Room temperature is sufficient but heat may be applied to shorten the reaction time. The reaction time is ordinarily in the range of 2-3 hours or more. Since the thiol group produced by the reduction is required not to be substantially oxidized, the reduction operation should conveniently be carried out in an atmosphere of inert gas to give good results.

The decomposition product thus obtained by the reduction of keratin material is then chemically modified at the thiol groups thereof to obtain a derivative thereof. The derivatives at the thiol groups include:

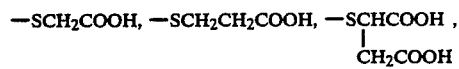

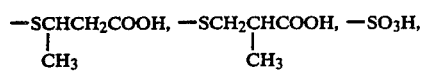

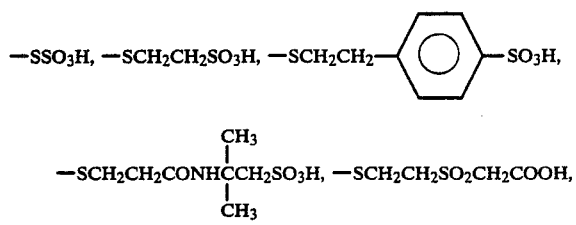

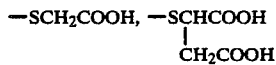

among which

are preferable.

The chemical modification of the thiol group is known per se and can be conducted, for example, based on procedures known from N. H. Leon; Textile Progress, Vol. 7, page 1 (1975), "Yuki Ioo Kagobutsu (Organic Sulfur Compounds)" written by Shigeru Daikyo and published by Kagaku Dojin (1968) and "Kobunshi Jikkengaku Koza" written by Masami Oku, Vol. 12, Kyoritsu Shuppan (1957). Typical methods are shown below.

1. Method utilizing the nucleophilic substitution reaction of SH group $$K-SH + R-L \longrightarrow K-S-R + HL$$

(in which K represents a residue of keratin compound, R represents a chemically modifying group to be introduced, and L represents an leaving atom or group such as a halogen atom or an acid residue). Compounds reacting by this method include, for example, halogen compounds such as iodoacetic acid, bromoacetic acid, chloroacetic acid and the like.

2. Method utilizing the nucleophilic addition reaction of SH group with a double bond existing between carbon atoms

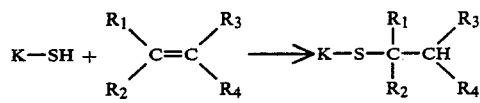

(in which at least one of $R_1$, $R_2$, $R_3$, and $R_4$ represents a carboxyl group or sulfonic acid group and the other represent an alkyl group or hydrogen atom, and K has the same meaning as defined hereinbefore).

Compounds reacting by this method include, for example, acrylic acid, methacrylic acid, crotonic acid, maleic acid, fumaric acid, vinyl cargoxymethylsulfone, vinylsulfonic acid, styrenesulfonic acid, 2-acrylamido-2-methylpropanesulfonic acid and the like.

3. Method using the substitution reaction between SH group and sulfite compound

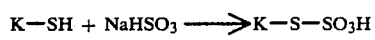

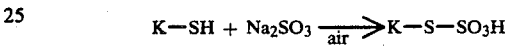

(in which K has same meaning as defined above).

4. Method of oxidizing SH group into sulfonic acid group

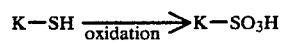

(in which K has the same meaning as defined hereinbefore).

The oxidizing agents used in this reaction include, for example, halogens, permanganates, and the like.

(3) Hydrolysis Reaction

1. Hydrolysis with Acid

Mentioned as acid are, for example, inorganic acids such as hydrochloric acid, sulfuric acid, phosphoric acid, nitric acid, hydrobromic acid and the like, and organic acids such as acetic acid, formic acid, oxalic acid and the like. These acids are generally employed at a concentration of 3-85% and it is desirable that the hydrolysis reaction is invariably caused to proceed at a pH of below 4. The reaction temperature is preferably in the range of 40°-100° C. though it may be raised up to 160° C. under pressure. The reaction time is conveniently in the range of 2-24 hours. The reaction product may be used as it is after neutralization with alkalis such as sodium hydroxide, sodium carbonate and ammonia or may be used after purification such as by gel filtration and ion exchange resins.

The product obtained by the hydrolysis with acid merely undergoes the hydrolysis at the polypeptide chain of keratin without involving any other changes, so that it shows better results than one obtained by hydrolysis with alkali.

2. Hydrolysis with Alkali

As alkalis there are used inorganic alkaline salts such as sodium hydroxide, potassium hydroxide, lithium hydroxide, barium hydroxide, sodium carbonate, potassium carbonate, lithium carbonate, sodium silicate, borax and the like. These are ordinarily used at a concentration of 1-20%. Larger amounts than as required are unfavorable since the hue of the solution of hydrolysate turns brown to black. The reaction is preferably conducted at room temperature to 100° C. for a time of 30 minutes to 24 hours. Care should be taken not to make the temperature higher and the reaction time longer than required. As the hydrolysis reaction with alkali proceeds, the hydrolysate of keratin dissolves with the attendant advantage that how far the reaction proceeds can be visibly observed. The reaction is completed at the time when the reaction mixture has turned into a uniform solution.

3. Hydrolysis with Enzyme

Examples of enzymes to be employed include acidic proteinases such as pepsin and the like, and neutral proteinases such as papain, bromelain, thermolysin, trypsin and chymotrypsin and the like. The pH at the time of the hydrolysis should preferably be controlled in the range of 1-3 for the acidic proteinases such as pepsin and in the range of 5-8 for the neutral proteinases such as papain. It is convenient that the pH is properly adjusted by the use of an ammonium acetate/ammonia buffer solution, a phosphoric acid buffer solution and the like buffer solutions. The reaction temperature is favorably in the range of 30°-45° C. and the reaction time is ordinarily in the range of 3-24 hours.

With the hydrolysis reaction with enzymes, the molecular weight of hydrolysate is greatly influenced by the amount of enzyme, reaction temperature and reaction time. Accordingly, in order to obtain a keratin hydrolysate with an intended molecular weight, it is necessary to check by the gel filtration technique a distribution of the molecular weight of hydrolysate in relation to variations in the amount of enzyme, reaction temperature and reaction time so as to empirically determine the optimum conditions.

The hydrolysates obtained from enzymes show a narrow distribution of molecular weight than hydrolysates obtained from acids or alkalis and contain reduced amounts of free amino acids, thus being more favorable for use as a cosmetic ingredient.

The hydrolysates are preferred to have the disulfide bonds in the structure thereof as much as possible. To this end, it is necessary that keratin materials used have high purity and that the hydrolysis reaction are conducted under mild conditions.

The decomposition products obtained by the method (1) or (2) should preferably have an average molecular weight of 30,000-100,000 and those obtained by the method (3) should preferably have an average molecular weight of 200-5,000.

The decomposition product obtained by the method (3) can be formulated as the decomposition derivative of keratin material in the pre-shampoo treatment according to the invention as it is since it is soluble in general polar solvents such as water, ethanol, methanol, ethylene glycol, propylene glycol, glycols and the like. However, the decomposition products obtained by the methods (1) and (2) are insoluble in polar solvents, so that it is necessary to add such products in the form of an alkali salt. Examples of the alkali salts include salts of alkali metals such as sodium, potassium and the like, ammonium salts, and salts of organic bases such as ethanolamine, diethanolamine, triethanolamine, 2-amino-2-methylpropanol, aminomercaptopropanediol, triisopropanolamine, glycine, histidine, alginine and the like. These salts may be prepared in a separate system and added to the pre-shampoo treatment, or the decomposition product obtained by oxidation of keratin material or reduction derivative of keratin material and an alkaline material may be added to the pre-shampoo treatment in which they are converted into an intended salt. In the latter case, the alkaline materials are, for example, inorganic alkaline materials such as sodium hydroxide, potassium hydroxide, sodium carbonate, potassium carbonate and the like, and organic alkaline materials such as ammonia, ethanolamine, diethanolamine, triethanolamine, 2-amino-2-methyl-1-propanol, 2-amino-2-methyl-1,3-propanediol, 2-amino-2-methyl-1-propanol, 2-amino-2-ethyl-1,3-propanediol, 2-amino-1-butanol, triisopropanolamine, diisopropanolamine, monoisopropanolamine, lysine, alginine, histidine, hydroxylysine and the like. Where the alkaline materials are added to the system to cause formation of a salt, the amount of the alkaline material is preferably in an amount of 0.1-8 equivalents of the carboxyl group or sulfonic acid group of the decomposition product obtained by the method (1) or (2).

The cationic polymers to be used in another modification of the present invention include polymeric materials of diallyl quaternary ammonium salts, cationic celluloses, cationic starches, and cationic vinyl polymers which are described in the following.

1. Polymeric materials of diallyl quaternary ammonium salts

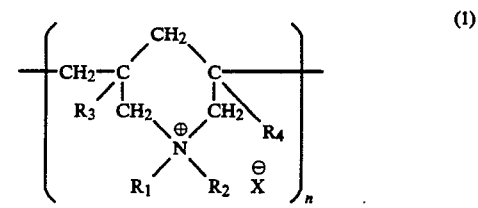

(1)

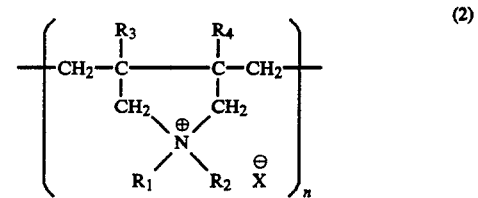

(2)

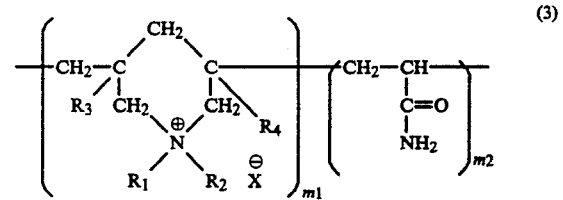

(3)

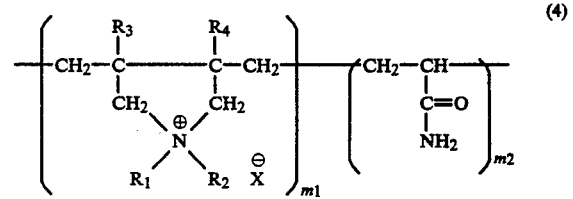

(4)

(in which $R_1$ and $R_2$ may be the same or different and represent hydrogen or an alkyl group having 1-18, preferably 1-4, carbon atoms, $R_3$ and $R_4$ may be the same or different and represent hydrogen, an alkyl group having 1-3 carbon atoms or a phenyl group, $X^{\ominus}$ represents a residue of an anion, e.g. a halogen ion such as chlorine, bromine or the like, a residue of an inorganic acid such as sulfuric acid, nitric acid or the like, or a residue of an organic acid such as methyl sulfuric acid, hydroxycarboxylic acid or the like, and n, $m_1$ and $m_2$ are values enough to give a molecular weight of 10,000–1,000,000).

2. Cationic celluloses or cationic starches $$A\text{\textendash}(O\text{\textendash}B\text{\textendash}\underset{R_7}{\overset{R_5}{N^\oplus}}\text{\textendash}R_6\cdot X^\ominus)_l \quad (5)$$

(in which

A: a residue of cellulose or starch,
B: an alkylene group or a hydroxyalkylene group,
$R_5$, $R_6$, $R_7$: They may be the same or different and represent an alkyl group, an aryl group, an aralkyl group or may form a hyterocyclic ring by combination with the nitrogen atom in the formula,
X: an anion (chlorine, bromine, iodine, sulfuric acid, sulfonic acid, methylsulfuric acid, phosphoric acid, nitric acid or the like)
l: a positive integer.

3. Cationic vinyl polymers $$\text{\textendash}(CH_2\text{\textendash}CH)_n\text{\textendash} \quad (6)$$

(with pyridinium ring, $N^\oplus$–$R_8$, substituent $R_9$, $X^\ominus$)

(in which $R_8$ and $R_9$ may be the same or different and represent hydrogen, an alkyl group having 1–6 carbon atoms or a phenyl group, and n and $X^\ominus$ have the same meanings as defined hereinbefore, respectively.

$$\text{\textendash}(CH_2\text{\textendash}\underset{\underset{O}{\overset{\|}{C}}\text{\textendash}Y\text{\textendash}(CH_2)_{m_3}\text{\textendash}N^\oplus(R_{11})(R_{12})(R_{13})\ X^\ominus}{\overset{R_{10}}{C}})_n\text{\textendash} \quad (7)$$

(in which $R_{10}$: a hydrogen atom or a methyl group,
$R_{11}$, $R_{12}$, $R_{13}$: They may the same or different and represent a hydrogen atom, an alkyl group having 1–4 carbon atoms, or a substituted alkyl group,
Y: an oxygen atom or an NH group in the amido bonding,
X: an anion,
$m_3$: an integer of 1 to 10,
n: having the same meaning as defined hereinbefore.

$$\text{\textendash}(CH_2\text{\textendash}CH)_n\text{\textendash} \quad (8)$$

(phenyl ring with $CH_2N^\oplus(R_{14})(R_{15})(R_{16})\ X^\ominus$)

(in which $R_{14}$, $R_{15}$, $R_{16}$: They are the same or different and represent a hydrogen atom, an alkyl group having 1 or 2 carbon atoms, or a substituted alkyl group.
X: an anion,
n: having the same meaning as defined hereinbefore.

Of these cationic polymers, diallyldimethylammonium homopolymer and cationic cellulose are preferable.

The pre-shampoo treatments according to one and another embodiments of the invention are not critical with respect to the amount of the decomposition derivative of keratin material but less amounts than 0.05 wt% (hereinafter referred to simply as %) are encountered with a difficulty in showing satisfactory effects of the invention whereas larger amounts than 5% are disadvantageous in that stickiness develops under high humidity conditions. Accordingly, the amount is preferably in the range of 0.05–5% of the composition.

In the second embodiment according to the invention, the amount of the cationic polymer is preferably in the range of 0.1–5% of the composition since less amounts than 0.1% are unfavorable in the sense that the effect of the polymer is not shown whereas larger amounts than 5% do not offer any further advantages.

In the second embodiment of the invention, the ratio by weight of the decomposition derivative of keratin material to the cationic polymer is generally in the range of 1:10–20:1, preferably 1:5–10:1.

The pre-shampoo treatment according to one embodiment of the invention can be prepared by dissolving or suspending the decomposition derivative of keratin material and other known components optionally added as required in a medium such as water. Likewise, the pre-shampoo treatment according to another embodiment of the invention can be prepared by dissolving or suspending the decomposition derivative of keratin material, cationic polymer and other known components optionally added as required in a medium such as water.

The known optional components include oils such as higher alcohols, fatty acid esters and the like, nonionic active agents serving as a emulsifiers or solubilizing agent such as polyoxyalkylene alkyl ethers, moisture-holding agents such as glycerine, pyrrolidonecarboxylic acids and the like. On using these additives, the feeling of finishing of the pre-shampoo treatment after treatment and washing of hair can be arbitrarily controlled. That is, the addition of a liquid oil component contributes to imparting suppleness to hair, the moisture-holding agents contribute to imparting the feeling of moistness to hair, and higher alcohols serve to impart the feeling of dryness.

The thus obtained pre-shampoo treatment according to one embodiment of the invention is incorporated with the decomposition derivatives of keratin material which show a better absorptivity on hair than other peptide compounds such as, for example, collagen, so that it shows good moisture retentivity accompanied by the effect of other polar groups, with the attendant advantages that hair can be finished supplely and that the pre-shampoo can impart good conditioning effects to hair without involving any dullness which is considered as an inherent disadvantage of known products. Further, the pre-shampoo treatment according to the second embodiment of the invention shows a more excellent conditioning effect when adsorbed on hair since cationic polymers with large moisture retentivity are contained together with the decomposition derivatives of keratin and especially shows an unexpectedly excellent conditioning effect on hair which has suffered damages.

The present invention is particularly described by way of Synthetic Examples and Examples, which should not be construed as limiting the present invention thereto.

SYNTHETIC EXAMPLE 1

Preparation of oxidation, decomposition derivatives of keratin materials:

(a) Ten grams of wool fibers were immersed in 700 g of 8% aqueous peracetic acid solution at room temperature for 1 day for the oxidation reaction. The resulting oxidized wool was filtered and washed with water, and then immersed in 700 g of a 0.1N ammoniacal solution at room temperature for 1 day, permitting about 90% of the wool to dissolve in the ammoniacal solution. About 1 g of the insoluble matters were removed by filtration and the aqueous ammoniacal solution of keratose to be an oxidized decomposition product of wool keratin was admixed with 2N hydrochloric acid to adjust pH to 4.0 whereupon $\alpha$-keratose was settled as a precipitate. This precipitate was filtered, washed with acetone and dried to obtain 5.4 g of $\alpha$-keratose.

(b) Wool fibers were heated under pressure in an autoclave by the use of saturated steam of 6 kg/cm$^2$ for 6 minutes and were abruptly released into the air to obtain a porous swollen matter. Ten grams of the swollen matter which had been reduced to pieces, 250 g of formic acid and 50 g of a 30% aqueous hydrogen peroxide solution were charged into a 500 ml three neck flask to immerse the pieces at room temperature for 1 day, whereupon no powder was found in the solution with the foam-like matter being floated on the upper layer. This reaction mixture was filtered and the filtrate was poured into 1.5 liters of water, followed by adding hydrochloric acid to adjust the pH to 4. The resulting precipitate was collected by filtration and washed with 500 ml of water to obtain 4.5 g of $\alpha$-keratose. To the insoluble matters from which the reaction product had been removed by filtration were added 350 ml of water and then an ammoniacal solution to adjust the pH to 11, and the matters were immersed at room temperature for 1 day. The system was filtered and the filtrate was added with hydrochloric acid to adjust the pH to 4. The resulting precipitate was collected by filtration to obtain 0.7 g of $\alpha$-keratose. It was found that 1.4 g of the insoluble matters was primarily made of $\beta$-keratose.

SYNTHETIC EXAMPLE 2

Preparation of reduced, decomposition derivatives of keratin materials:

(a) Ten grams of wool fibers were immersed in 600 ml of an aqueous solution with concentrations of 8M urea and 0.01M Tris buffer, to which was added 6 ml of 2-mercaptoethanol, followed by adjusting the pH to 10 by means of a 5N potassium hydroxide aqueous solution to conduct the reduction reaction in a stream of nitrogen at room temperature. About 3 hours after commencement of the reaction, the wool was allowed to dissolve in the reaction solution in an amount of about 85% thereof. While the system was adjusted with a 5N potassium hydroxide aqueous solution so as not to permit the pH below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against deionized water to remove low molecular weight impurities including urea. As the urea was dialyzed, the content in the cellulose tube turned white since HGT (component with high contents of glycine and tyrosine) to be a waterinsoluble component was allowed to percipitate. After completion of the dialysis, the HGT was removed by centrifugal separation and S-carboxymethyl keratin (SCMKA) was obtained from the neutral transparent aqueous solution of SCMKA by the isoelectric precipitation method. That is, 1N hydrochloric acid was added to the system to adjust its pH to 4.4 by which SCMKA turned insoluble and separated as precipitate. This precipitate was filtered, washed with ethanol and dried to obtain 4.2 g of SCMKA.

(b) The procedure of Synthetic Example 2-(a) was repeated except that there were used instead of wool fibers feathers which were heated for 6 minutes in an autoclave by means of superheated steam of 6 kg/cm$^2$ and 240° C. and then abruptly released into the air to obtain a porous swollen matter and that 1.75 g of maleic acid was used instead of iodoacetic acid, thereby obtaining 5.3 g of S-(1,2-dicarboxyethyl)-keratin.

(c) The procedure of Synthetic Example 2-(a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Synthetic Example 2-(a) was repeated using 28 g of styrenesulfonic acid instead of iodoacetic acid, thereby obtaining 4.8 g of S-(sulfophenylvinyl)-keratin.

(e) Eight grams of wool fibers were dispersed in 300 ml of n-propanol and 300 ml of a 0.1N Tris buffer solution. After substitution with nitrogen, 3.2 ml of tri-n-butylphosphine was added, followed by agitating at room temperature for 24 hours. After the solution was subjected to filtration, to the insoluble matters were added 400 ml of water, 9.28 g of maleic acid and about 30 ml of 5N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated at room temperature for 18 hours. The reaction solution was filtered to remove impurities therefrom and the resultant filtrate was placed in a cellulose tube in which it was dialyzed against ion-exchanged water to remove low molecular weight impurities therefrom. After completion of the dialysis, the insoluble matters in the cellulose tube were removed by centrifugal separation and the neutral transparent aqueous solution was adjusted to have a pH of 4.4 by addition of about 5.5 ml of 1N hydrochloric acid and the resulting precipitate was collected by filtration, followed by washing with ethanol and drying to obtain 3.9 g of S-(1,2-dicarboxyethyl)-keratin.

(f) The procedure of Synthetic Example 2-(e) was repeated except that there was used instead of wool fibers a powder of a porous swollen matter which was obtained by heating wool in an autoclave by means of saturated steam of 6 kg/cm$^2$ for 6 minutes and that 16.5 f of 2-acrylamido-2-methylpropane-sulfonic acid ws used instead of maleic acid, thereby obtaining 4.5 g of keratin-S-(2-acrylamido-2-methylpropane-sulfonic acid).

SYNTHETIC EXAMPLE 3

Preparation of Hydrolysis derivatives of keratin materials:

(a) Ten grams of wool fibers were immersed in 300 g of a 1% sodium hydrogensulfite aqueous solution, whose pH was then adjusted to 6.7 by means of a 5N aqueous caustic soda solution. Thereafter, 0.2 g of papain was added to the system to conduct the hydrolysis reaction at 60° C. for 15 hours, by which about 80% of the wool was allowed to dissolve in. Insoluble portion were removed by filtration and the sulfite contained in the resultant filtrate was removed by the use of a membrane with a fractional molecular weight of 500. The aqueous solution of the hydrolysate was concentrated and freeze dried to obtain 7.7 g of the hydrolysate having a molecular weight of 500–2000.

(b) Ten grams of wool fibers were immersed in 300 g of a 75% phosphoric acid aqueous solution and the hydrolysis reaction was conducted at 120°–130° C. for 5 hours. The reaction system was cooled and filtered to remove insoluble matters therefrom, to which was added water of 4–5 times in volume of the filtrate to further remove insoluble matters. Then, calcium carbonate or barium hydroxide was added to the filtrate to adjust its pH to 6.7, after which the resulting precipitate was collected by filtration and dried to obtain 8.0 g of a hydrolysate having a molecular weight of 500–2000.

Note: The amount of S—S bonds in the hydrolysate obtained by the procedure of Synthetic Example 3-(a) or 3-(b) was 50 moles per $10^5$ g of the hydrolysate, revealing that little or no cystine in the wool was destroyed during the course of the hydrolysis.

(c) One hundred grams of feathers were heated under pressure in an autoclave for 6 minutes by the use of superheated steam of 6 kg/cm$^2$ and 240° C., and then abruptly released in the air to obtain a porous swollen matter. This matter was reduced into pieces, to which was added 3 l of 0.3N caustic soda for conducting the hydrolysis reaction at 60° C. for 18 hours, followed by neutralizing with 1N hydrochloric acid and filtering the reaction solution. The sodium chloride in the resulting filtrate was removed by the ultrafiltration method using a membrane with a fractional molecular weight of 500. The aqueous solution of the hydrolysate of the keratin was concentrated and freeze dried to obtain 7.2 g of the hydrolysate of keratin. The molecular weight of the hydrolysate was found to be 1,800 when determined by the gel filtration method.

(d) 100 g of pieces of hoof of horse with a uniform size of 0.25–1 mm were defatted with a 50% methanol and 50% chloroform solution and then treated with 1% ammoniacal solution to remove soluble proteins therefrom, which was then placed in a three neck flask, followed by adding 20 g of sodium hydroxide and 400 g of deionized water and subjecting to the hydrolysis reaction at 90° C. for 4 hours while agitating. After cooling, hydrochloric acid was added to adjust the pH of the system to 8 and then the reaction solution was filtered. The sodium chloride in the filtrate was removed, followed by repeating the procedure of Synthetic Example 3-(c) to obtain 68 g of a hydrolysate of keratin. This hydrolysate had a molecular weight of 2,500 when measured by the gel filtration method.

EXAMPLE 1

Pre-shampoo treatments of the following formulations were prepared using decomposition derivatives of keratin materials to evaluate their performance. The results are shown in Table 2.

Formulation:

| | |
|---|---|
| Decomposition derivatives of keratin materials (those shown in Table 1) | (Table 1) |
| Lauryl alcohol | 2.0% |
| Polyoxyethylene (15) nonyl phenyl ether | 0.5 |
| Hydroxyethyl cellulose | 0.5 |
| Ethanol | 5.0 |
| Triethanolamine | (Table 1) |

Evaluation method:

(1) Feeling of hair during washing

Tresses which had been made of hair of Japanese female with a length of 20 cm and a weight of 20 g were each applied with 2 g of each of pre-shampoo treatments. After having allowed to stand for 5 minutes, the hair was applied with 2 g of a commercially available plain shampoo and lathered as usual for 1 minute, whereupon the feeling of the hair was evaluated. The evaluation was made by a paired comparison test in which a tress treated with a commercially available pre-shampoo hair treatment mainly composed of lanolin was used as a control.

(The evaluation was indicated by an average value of an expert panel consisting of 20 members.)

| Evaluation Point | Evaluation |
|---|---|
| +2 | Better feeling than that of the control hair tress. |
| +1 | Slightly better feeling than that of the control hair tress. |
| 0 | Feeling equal to that of the control hair tress. |
| −1 | Slightly poorer feeling than that of the control hair tress. |
| −2 | Poorer feeling than that of the control hair tress. |

(2) Feeling of Hair in state

After completion of the evaluation of the feeling of the hair during washing, it was washed with running water of 40° C. for 1 minute and was dried with a towel to remove excess water. The stress was evaluated similarly to the tress during washing to know the feeling in a wet state.

(3) Felling and combing ease after drying

After the evaluation of (2), the wet hair tresses were each air dried and its feeling was evaluated in accordance with the method of (2). Then, the combing ease was evaluated similarly to the method of (1) using a commercially available nylon comb.

TABLE 1

| Sample No. | Decomposition derivative of keratin material | Amount | Amount of triethanolamine |
|---|---|---|---|
| 1 | decomposition derivative of keratin material of Synthetic Example 1-(a) | 0.1% | 0.01% |
| 2 | decomposition derivative of keratin material of Synthetic Example 1-(a) | 0.5 | 0.05 |
| 3 | decomposition derivative of keratin material of Synthetic Example 1-(a) | 2.0 | 0.1 |
| 4 | decomposition derivative of keratin material of Synthetic Example 1-(a) | 5.0 | 0.5 |
| 5 | decomposition derivative of keratin material of Synthetic Example 1-(b) | 2.0 | 0.2 |
| 6 | decomposition derivative of keratin material of Synthetic | 2.0 | 0.2 |

TABLE 1-continued

| Sample No. | Decomposition derivative of keratin material | Amount | Amount of triethanolamine |
|---|---|---|---|
| 7 | Example 2-(a) decomposition derivative of keratin material of Synthetic Example 2-(b) | 0.1 | 0.01 |
| 8 | decomposition derivative of keratin material of Synthetic Example 2-(b) | 0.5 | 0.05 |
| 9 | decomposition derivative of keratin material of Synthetic Example 2-(b) | 2.0 | 0.2 |
| 10 | decomposition derivative of keratin material of Synthetic Example 2-(b) | 5.0 | 0.5 |
| 11 | decomposition derivative of keratin material of Synthetic Example 2-(c) | 2.0 | 0.2 |
| 12 | decomposition derivative of keratin material of Synthetic Example 2-(d) | 2.0 | 0.2 |
| 13 | decomposition derivative of keratin material of Synthetic Example 2-(e) | 2.0 | 0.2 |
| 14 | decomposition derivative of keratin material of Synthetic Example 2-(f) | 2.0 | 0.2 |
| 15 | decomposition derivative of keratin material of Synthetic Example 3-(a) | 3.0 | 0 |
| 16 | decomposition derivative of keratin material of Synthetic Example 3-(b) | 2.0 | 0 |
| 17 | decomposition derivative of keratin material of Synthetic Example 3-(c) | 3.0 | 0 |
| 18 | decomposition derivative of keratin material of Synthetic Example 3-(d) | 3.0 | 0 |
| Comparative Product 1 | derivative obtained by decomposition of collagen with acid (M.W. 10,000–20,000) | 2.0 | 0 |
| Comparative Product 2 | derivative obtained by decomposition of collagen with alkali (M.W. 800–1,000) | 3.0 | 0 |
| Control 1 | nil | 0 | 0 |

Results:

TABLE 2

| Sample No. | Feeling of Hair during washing | Feeling of Hair after washing | Feeling of Hair after drying | Combing Ease (after drying) |
|---|---|---|---|---|
| 1 | +0.9 | +1.0 | +0.9 | +0.8 |
| 2 | +1.1 | +1.2 | +1.2 | +1.1 |
| 3 | +1.3 | +1.4 | +1.4 | +1.3 |
| 4 | +1.4 | +1.4 | +1.4 | +1.4 |
| 5 | +1.3 | +1.3 | +1.3 | +1.4 |
| 6 | +1.3 | +1.4 | +1.3 | +1.3 |
| 7 | +0.9 | +0.9 | +1.0 | +0.9 |
| 8 | +1.1 | +1.1 | +1.2 | +1.2 |
| 9 | +1.3 | +1.4 | +1.3 | +1.4 |
| 10 | +1.4 | +1.4 | +1.4 | +1.3 |
| 11 | +1.0 | +1.1 | +1.1 | +1.0 |
| 12 | +1.3 | +1.4 | +1.4 | +1.4 |
| 13 | +1.3 | +1.4 | +1.3 | +1.4 |
| 14 | +1.4 | +1.4 | +1.3 | +1.4 |
| 15 | +0.5 | +0.6 | +0.5 | +0.6 |
| 16 | +1.2 | +1.3 | +1.2 | +1.1 |
| 17 | +1.2 | +1.2 | +1.3 | +1.2 |
| 18 | +0.4 | +0.5 | +0.4 | +0.4 |
| Comparative Product 1 | +1.2 | +1.3 | +1.3 | +1.3 |
| Comparative Product 2 | +0.3 | +0.4 | +0.4 | +0.3 |
| Control 1 | 0 | 0 | 0 | 0 |

EXAMPLE 2

Pre-shampoo treatments having the following formulations were prepared using decomposition derivatives of keratin materials and polymers having cyclic cationic groups therein and their performance was evaluated in accordance with the method of Example 1. The results are shown in Table 4.

Formulation:

| | |
|---|---|
| Poly(dimethyldiallylammonium chloride) (M.W. 100,000) | 1.0% |
| Decomposition derivatives of keratin materials (Table 3) | (Table 3) |
| Polyoxyethylene (10) oleyl ether | 2.0 |
| Hydroxyethyl cellulose | 0.5 |
| Propylene glycol | 5.0 |
| Triethanolamine | (Table 3) |

TABLE 3

| Sample No. | Decomposition derivative of keratin material | Amount | Amount of triethanolamine |
|---|---|---|---|
| 1 | decomposition derivative of keratin material of Synthetic Example 1-(a) | 0.1% | 0.01% |
| 2 | decomposition derivative of keratin material of Synthetic Example 1-(a) | 0.5 | 0.05 |
| 3 | decomposition derivative of keratin material of Synthetic Example 1-(a) | 1.0 | 0.1 |
| 4 | decomposition derivative of keratin material of Synthetic Example 1-(a) | 2.0 | 0.2 |
| 5 | decomposition derivative of keratin material of Synthetic Example 1-(a) | 5.0 | 0.5 |
| 6 | decomposition derivative of keratin material of Synthetic Example 1-(b) | 2.0 | 1.0 |
| 7 | decomposition derivative of keratin material of Synthetic Example 2-(a) | 2.0 | 0.3 |
| 8 | decomposition derivative of keratin material of Synthetic Example 2-(b) | 2.0 | 0.3 |
| 9 | decomposition derivative of keratin material of Synthetic Example 2-(c) | 2.0 | 0.3 |
| 10 | decomposition derivative of keratin material of Synthetic Example 2-(d) | 2.0 | 0.3 |
| 11 | decomposition derivative of keratin material of Synthetic Example 2-(e) | 2.0 | 0.3 |
| 12 | decomposition derivative of keratin material of Synthetic Example 2-(f) | 2.0 | 0.3 |
| 13 | decomposition derivative of keratin material of Synthetic Example 3-(a) | 3.0 | 0 |
| 14 | decomposition derivative of keratin material of Synthetic Example 3-(b) | 2.0 | 0 |
| 15 | decomposition derivative of keratin material of Synthetic Example 3-(c) | 3.0 | 0 |
| 16 | decomposition derivative of keratin material of Synthetic Example 3-(d) | 3.0 | 0 |

TABLE 2-continued

| Sample No. | Feeling of Hair during washing | Feeling of Hair after washing | Feeling of Hair after drying | Combing Ease (after drying) |
|---|---|---|---|---|
| Control 1 | 0 | 0 | 0 | 0 |

TABLE 3-continued

| Sample No. | Decomposition derivative of keratin material | Amount | Amount of triethanolamine |
|---|---|---|---|
| Control 1 | nil | 0 | 0 |

Results:

TABLE 4

| Sample No. | Feeling of Hair during washing | Feeling of Hair after washing in wet state | Feeling of Hair after drying | Combing Ease (after drying) |
|---|---|---|---|---|
| 1 | +1.1 | +1.2 | +1.3 | +1.2 |
| 2 | +1.4 | +1.5 | +1.5 | +1.4 |
| 3 | +1.6 | +1.6 | +1.5 | +1.5 |
| 4 | +1.7 | +1.7 | +1.6 | +1.6 |
| 5 | +1.8 | +1.8 | +1.7 | +1.6 |
| 6 | +1.8 | +1.7 | +1.7 | +1.7 |
| 7 | +1.7 | +1.7 | +1.8 | +1.7 |
| 8 | +1.8 | +1.8 | +1.8 | +1.8 |
| 9 | +1.4 | +1.5 | +1.5 | +1.3 |
| 10 | +1.7 | +1.7 | +1.7 | +1.7 |
| 11 | +1.8 | +1.7 | +1.8 | +1.6 |
| 12 | +1.7 | +1.7 | +1.8 | +1.6 |
| 13 | +1.8 | +1.7 | +1.6 | +1.6 |
| 14 | +1.7 | +1.7 | +1.7 | +1.8 |
| 15 | +1.7 | +1.8 | +1.8 | +1.7 |
| 16 | +1.3 | +1.2 | +1.4 | +1.3 |
| Control 1 | +0.6 | +0.7 | +0.7 | +0.6 |
| No treatment | −0.3 | 0 | 0 | 0 |

EXAMPLE 3

Pre-shampoo treatment compositions of the following formulations were prepared using the decomposition derivatives of keratin materials prepared in Synthetic Example 3-(b) and the cationic polymers shown in Table 5 and their performance was evaluated in accordance with the method of Example 1. The results are shown in Table 6.

Formulation:

| | |
|---|---|
| Decomposition derivative of keratin materials (Synthetic Example 3-(b)) | 2.0% |
| Cationic polymers (Table 5) | (Table 5) |
| Polyoxyethylene (20) nonyl phenyl ether | 2.0 |
| Methyl cellulose | 0.3 |
| Propylene glycol | 5.0 |

TABLE 5

| Sample No. | Cationic Polymer | Amount (%) |
|---|---|---|
| 1 | poly(dimethyl piperidinium chloride) structure, $n_4$ (average M.W. 100,000) | 0.5 |
| 2 | poly(dimethyl piperidinium chloride) structure, $n_4$ (average M.W. 100,000) | 1.0 |
| 3 | poly(dimethyl piperidinium chloride) structure, $n_4$ (average M.W. 100,000) | 2.0 |
| 4 | $+CH_2-CH+_{n_2}-$ with phenyl-$CH_2NMe_3.Cl^\ominus$ (average M.W. 20,000) | 1.0 |
| 5 | $+CH_2-CH+_{n_3}-$ with N-methylpyridinium$.Cl^\ominus$ (average M.W. 20,000) | 1.0 |
| 6 | cationic cellulose (Polymer JR-400, made by UCC CO., LTD) | 1.0 |
| 7 | cationic cellulose (Polymer JR-400, made by UCC CO., LTD) | 2.0 |
| 8 | $+CH_2-C(CH_3)+_{n_4}-$ $COOCH_2CH_2NMe_3.Cl^\ominus$ (average M.W. 1,000,000) | 0.5 |
| 9 | $+CH_2-C(CH_3)+_{n_4}-$ $COOCH_2CH_2NMe_3.Cl^\ominus$ (average M.W. 1,000,000) | 1.0 |
| 10 | $+CH_2-C(CH_3)+_{n_4}-$ $COOCH_2CH_2NMe_3.Cl^\ominus$ (average M.W. 1,000,000) | 2.0 |
| 11 | cationic product of vinylpyrrolidone-dimethylaminoethylmethacrylate copolymer (GAF Coat 734; made by GAF CO., LTD.) | 1.0 |
| 12 | aminoethyl acrylate-methacrylic acid-methacrylic ester copolymer (Cartolex L: National Starch Co., Ltd.) | 1.0 |
| 13 | $+N^\oplus(Me)_2-(CH_2CH_2O)_2CH_2CH_2-N^\oplus(Me)_2-CH_2COOCH_2OCOCH_2+_{n_5}$ $2Cl^\ominus$ (average M.W. 100,000) | 1.0 |
| 14 | cationic starch (the average number of | 1.0 |

TABLE 5-continued

| Sample No. | Cationic Polymer | Amount (%) |
|---|---|---|
|  | cationic groups introduced per anhydrous glucose unit is 0.30 and the viscosity of its 1% aqueous solution at 50° C. is 30 centipoises) |  |
| 15 | nil | 0 |

Results:

TABLE 6

| Sample No. | Feeling of Hair | | | Combing Ease (after drying) |
|---|---|---|---|---|
|  | during washing | after washing in wet state | after drying |  |
| 1 | +1.7 | +1.7 | +1.7 | +1.7 |
| 2 | +1.7 | +1.8 | +1.7 | +1.8 |
| 3 | +1.8 | +1.8 | +1.8 | +1.8 |
| 4 | +1.6 | +1.6 | +1.6 | +1.5 |
| 5 | +1.6 | +1.5 | +1.6 | +1.6 |
| 6 | +1.8 | +1.8 | +1.8 | +1.8 |
| 7 | +1.8 | +1.8 | +1.8 | +1.8 |
| 8 | +1.5 | +1.5 | +1.4 | +1.4 |
| 9 | +1.6 | +1.6 | +1.5 | +1.4 |
| 10 | +1.7 | +1.6 | +1.6 | +1.5 |
| 11 | +1.5 | +1.5 | +1.5 | +1.4 |
| 12 | +1.5 | +1.5 | +1.5 | +1.5 |
| 13 | +1.6 | +1.7 | +1.6 | +1.7 |
| 14 | +1.4 | +1.5 | +1.4 | +1.3 |
| 15 | +0.4 | +0.7 | +0.8 | +0.4 |
| No treatment | −0.3 | 0 | 0 | 0 |

What is claimed is:

1. A pre-shampoo hair treatment composition which comprises
   (A) 0.5–5% by weight of at least one decomposition derivative of keratin material selected from the group consisting of
      (1) alkali salts of decomposition products obtained by oxidation of keratin material, and
      (2) alkali salts of derivatives at the thiol group of decomposition products obtained by reduction of keratin material, alone or in combination with a keratin product having only been subjected to hydrolysis, and
   (B) 0.1 to 5 wt% of at least one cationic polymer selected from the group consisting of diallyl quaternary ammonium salts, cationic celluloses, cationic starches and cationic vinyl polymers; in a polar solvent.

2. A pre-shampoo type hair treatment composition according to claim 1, wherein said cationic polymer is diallyldimethylammonium homopolymer.

3. A pre-shampoo type hair treatment composition according to claim 1, wherein said cationic polymer is cationic cellulose.

4. A pre-shampoo type hair treatment composition according to claim 1, wherein the ratio by weight of said decomposition derivative to the cationic polymer is in the range of 1:10 to 20:1.

5. A pre-shampoo type hair treatment composition according to claim 4, wherein the ratio is in the range of 1:5 to 10:1.

* * * * *